Figure 1:
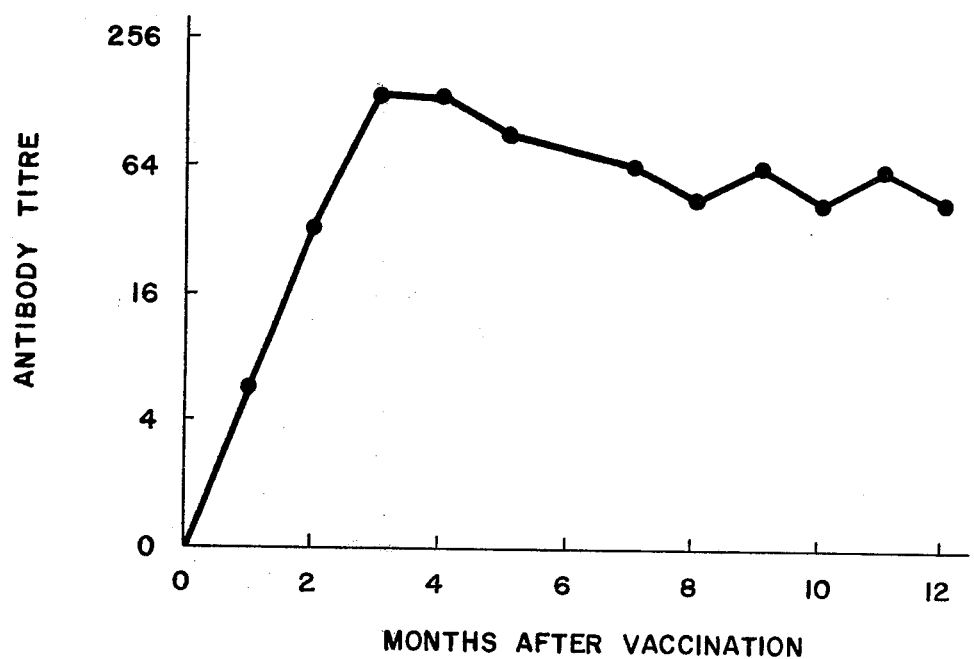
Figure 2:
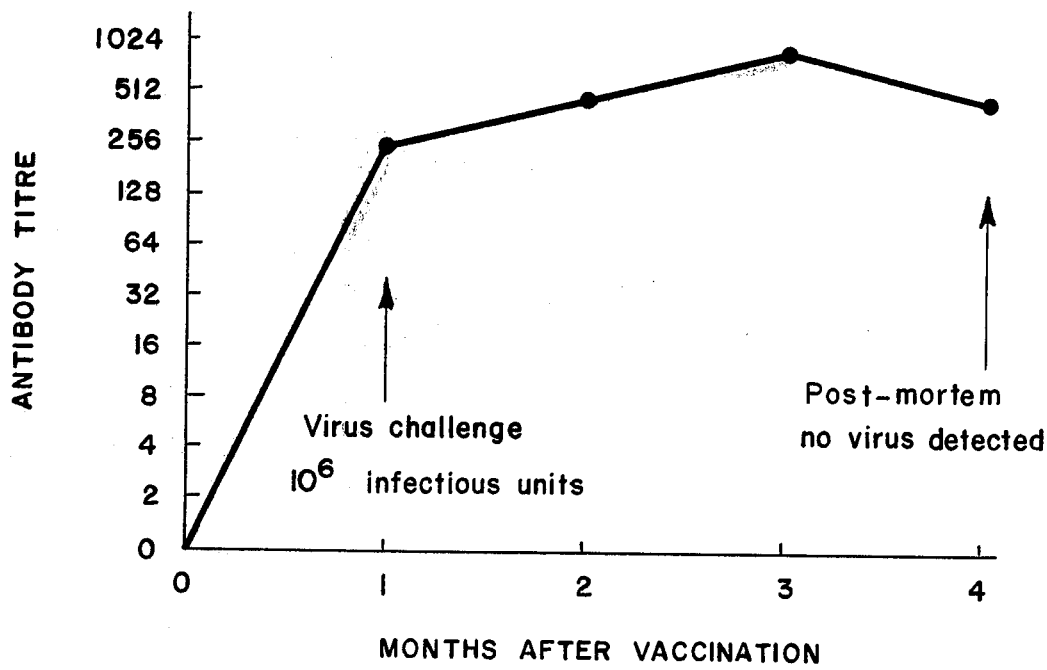
Figure 3:
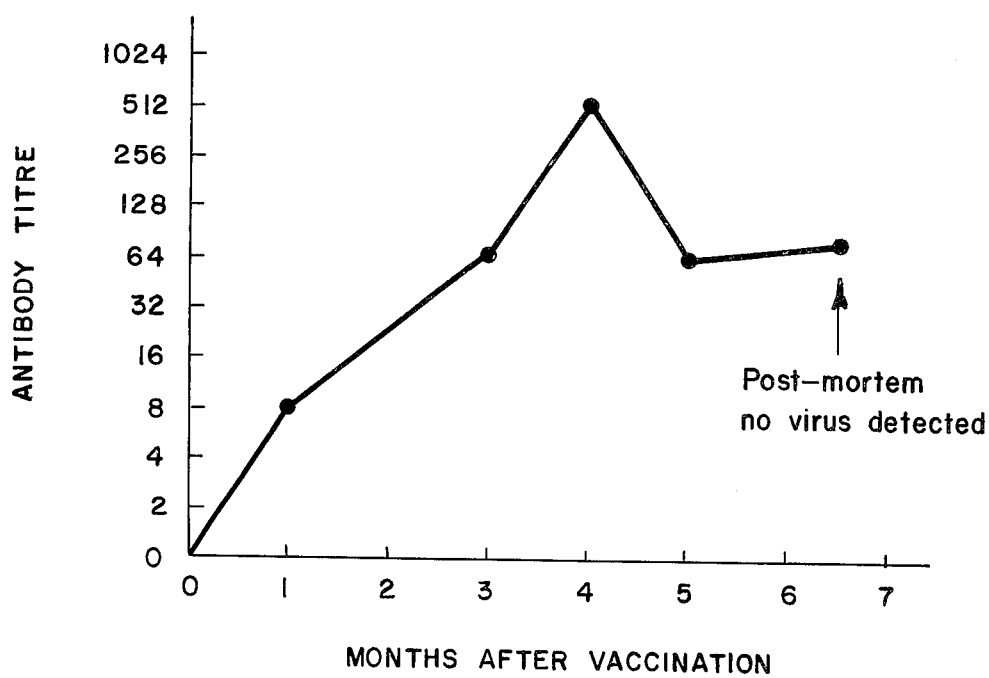

United States Patent [19]
Jarrett et al.

[11] 3,966,907
[45] June 29, 1976

[54] VACCINES AGAINST FELINE LEUKEMIA

[75] Inventors: William Fleming Hoggan Jarrett; James Oswald Jarrett; Lindsay Joan Mackey, all of Glasgow, Scotland

[73] Assignee: University of Glasgow, Glasgow, Scotland

[22] Filed: Sept. 13, 1974

[21] Appl. No.: 505,625

[30] Foreign Application Priority Data
Sept. 18, 1973 United Kingdom............... 43642/73

[52] U.S. Cl.................................... 424/89; 195/1.1
[51] Int. Cl.²......................................... A61K 39/12
[58] Field of Search........................ 424/89; 195/1.1

[56] References Cited
OTHER PUBLICATIONS

Vet. Bull. 41, No. 342, No. 5885, No. 5886, No. 6471, No. 6472, No. 6475, No. 6479, (1971).
Vet. Bull. 42, No. 2835, No. 6472, No. 70555, No. 4108, No. 4109, No. 5814, (1972).
Vet Bull. 34, No. 3400, No. 3401, (1964).
Vet Bull. 43, No. 328, No. 329, No. 330, No. 827, No. 1709, No. 1710, No. 2230, No. 2610, No. 3009, No. 3536, No. 3537, No. 3538, No. 5145, No. 5146, No. 5536, (1973).
Hardy et al., Nature 244: 266–269, Aug. 3, 1973, "Horizontal Transmission of Feline Leukemia Virus."
Essex, Ancology 26: 345–356, (1972), "Can Feline Oncornaviruses Cause Leukemia in Man"
Bross et al., Am. Jl. Pub. Health 62(11): 1520–1531, (1972), "Pets and Adult Leukemia."
Bross et al., J. Med. 1: 180–187, (1970), "Cats and Childhood Leukemia."

*Primary Examiner*—Shep K. Rose
*Attorney, Agent, or Firm*—Elliot N. Schubert; John J. McDonnell

[57] ABSTRACT

Vaccines affording protection against the diseases resulting from infection of cats with feline leukemia virus are produced from cells infected with that virus or from the virus alone.

4 Claims, 4 Drawing Figures

VACCINES AGAINST FELINE LEUKEMIA

The present invention relates to a vaccine and particularly to a vaccine offering protection against the diseases associated with the infection of cats with feline leukemia virus (FeLV).

It is known that feline leukemia virus may be transmitted between individual cats, thereby causing infection by the virus of a relatively high proportion of cats in a colony or in a population. It is thought that infection of cats with feline leukemia virus is responsible for diseases other than leukemia, for example immunosuppression and non-responsive anemias. The present invention provides vaccines and immunizing procedures which produce, in cats, high titres of antibody against FeLV associated antigens and protection of the animals against infection with this virus. Vaccines will be described which provide high titres of antibody against FeLV associated antigens in the blood of cats in the absence of any lasting virus infections. Methos will also be described of providing sufficient primary immunization against FeLV to enable a cat which is subsequently infected by the virus to mount a secondary response and thereby overcome the infection. In all cases, it is shown that the vaccines of the present invention provide sufficient protection for an animal to enable it to overcome a subsequent infection wwith FeLV, without inducing a lasting infection in the animal. In many cases, protection is achieved without the injection of infective materials.

The vaccines of the present invention may comprise preparations of cells, infected with FeLV, or preparations of the virus alone which has been separated from the cells in which it is grown. In both cases, the virus may be grown in a variety of different cells and cultured by conventional means. Thus, feline lymphoblasts may be cultured in suspension and these cells may transmit the virus particles from generation to generation. Similar cell cultures may be derived from cells of a non-feline species such as a dog or human being and these too may carry the virus infection from generation to generation. Alternatively, it is possible to culture feline embryo cells in monolayers. These cells may be infected and collected after a suitable period of infection. Cells from non-feline species may also be cultured in monolayers and infected. It is further possible to maintain tumor cells from an infected cat in continuous culture. It is found that the virus particles from such cells may display only low infectivity for cats while remaining capable of immunizing cats against infection with a fully-infective virus. In all cases, the culture of these cells is achieved using conventional conditions which provide for the replication of the virus.

It has now been found that cells infected with FeLV produce large quantities of virus-associated antigen on the surface of the cell membrane and that this membrane antigen is immunogenic. Antibodies raised in a cat by injection of infected cells are therefore active against cells in the animal which are infected with the virus. Such antibodies are also active against cells which have become infected and transformed into malignant tumor cells. However, it is also recognized that the virus particles themselves are immunogenic and can form the basis of an effective vaccine. Such a vaccine will be active against infecting virus particles rather than infected cells but both vaccines are considered to be within the scope of the present invention.

The vaccines of the present invention may therefore comprise infected cells or virus separated from infected cells and each may be presented to the animal in a variety of forms.

Thus, whole live cells which have been infected with FeLV and which have on their surfaces large amounts of virus-associated antigen may be administered to the animals. By selection of a suitable dose of cells, it is possible to obtain high titres of antibody against the virus or virus-infected cells without the retention of any live virus in the animal. The administration of infected cells to an animal naturally carries the risk of infecting the animal itself. However, by selecting the dose of the cells to be administered, it is possible to obtain immunization without lasting infections.

It is naturally preferred that non-infective materal should be used as a vaccine providing it is sufficiently immunogenic. Whole cells may be either rendered inactive by suppression of their growth or killed by a large number of treatments already known in the art. For example, live cells may be rendered inactive by treatment with RNA/DNA transcription and translation inhibitors such as mitomycin D. Alternatively, infected cells may be killed by, for example, irradiation, hydroxylamine or thermal inactivation. Two preferred agents for killing infected cells are paraformaldehyde and acetylethyleneimine, used either separately or in conjunction with one another. In all cases, the conditions used for killing the infected cells should be sufficient to substantially destroy their infective activity without removing their immunogenic properties.

When using paraformaldehyde as an agent to kill infected cells, the concentration and period of incubation should be such that substantially all of the cells are killed without an unacceptable reduction in their immunogenic activity. Similar agents to those described above may also be used in order to kill the live virus separated from the cell cultures, although the exact conditions used to kill the virus may differ from those used to kill cell-virus mixtures.

Conventional adjuvants may be added to the immunogenic material comprising the vaccine, in order to stabilize the material and enhance the immune reaction against it. Among these adjuvants suitable for this purpose, are Freund's complete or incomplete adjuvant, killed hemophilus pertussis or polynucleotide compositions. The preferred proportion of adjuvant may be established by experimentation.

The immunogenic material used in the present vaccines may be presented to the animal in any conventional formulation. For example, it may be suspended in a buffer solution in which its activity is preserved, freeze-dried, or maintained as a frozen suspension. The vaccine, in a suitable form for administration, may be injected into the animal by any suitable route. For practical reasons, the subcutaneous or intra-muscular routes are preferred.

It is possible by means of the present invention to provide immunity in an animal with a single administration of a suitable vaccine. Alternatively, it is possible to produce a primary response by an initial injection and a subsequent strong secondary response by a further injection at a later date. The former procedure is preferred as the animal need only be vaccinated on one occasion. It is further possible to provide a primary response with a single injection of vaccine, such that a subsequent natural infection of the animal will then result in a strong secondary reaction to the infection which will be sufficient to reverse the infection causing the reaction and thus to prevent the animal from contracting any of the diseases associated with infection by FeLV. It is shown below that the use of the present vaccines allow all of these procedures to be used successfully.

EXAMLE 1

Vaccination of cats with live cells infected with FeLV provide high titres, in the blood of these animals, of antibodies against FelV associated antigens. When high doses of cells are administered, the virus persists in the blood although no symptoms of disease are manifest. However, with lower doses of cells, infected with virus of lower infectivity, all trace of virus are removed from the blood within one month and high antibody titres are maintained, thus protecting the animal against subsequent infection by the virus.

Monolayer cultures of feline embryo fibroblasts are grown according to conventional procedures. The cells are chronically infected with FeLV of known sub groups. The infected cells were grown for sufficient time to allow extensive replication of the virus. They are then harvested, suspended in buffer at a known concentration of cells, packed by centrifugation and injected subcutaneously.

The animals are monitored each month for antibody to feline leukemia virus cell membrane antigen. At the end of the period of study, the animals were sacrificed and their tissues analyzed, by the procedures below, for the presence of live virus.

a. Samples from many different tissues are viewed with an electron microscope for the presence of visible virus particles.

b. Tissues from the animals are cultured in the presence of uninfected monolayer cells for 28 days. They are subsequently examined with an electron microscope scope and by immunofluorescence for the presence of virus particles and virus antigen. The results of immunization with live, infected cells are shown in the Table below.

TABLE 1

| Cells | | Average Peak Antibody Titre | Duration Study (months) | Virus Isolation at necropsy | Virus Subgroup |
|---|---|---|---|---|---|
| Type | Number | | | | |
| FEA | $2 \times 10^9$ | 120 | 6 – 13 | + | A + B |
| FEA | $7 \times 10^8$ | 96 | 6 | + | A |
| FEA | $4 \times 10^7$ | 202 | 1 – 3 | – | A + B + C |
| FL | $4 \times 10^7$ | 248 | 1 – 3 | – | A + B + C |

FEA Monolayer feline embryo fibroblasts.
FL Suspension feline lymphoblasts.

All cats immunized with live infected cells subsequently develop high titres of antibodies against FeLV associated antigens. When high doses of cells are injected, the presence of virus in the tissues persists for 6 to 12 months although no symptoms of disease were apparent. In contrast, immunization with lower doses of cells also result in the development of high antibody titres but no virus is detectable in these animals after a period of 1 to 3 months.

The rate of development of antibodies and their persistence in the blood is shown in FIG. 1. Animals are injected with $2 \times 10^9$ FEA cells and the level of antibodies in the blood monitored each month. It can be seen that a maximum antibody titre is reached within 3 months and that this persists at a high level beyond 12 months. It is therefore possible by selection of the dose of cells injected to immunize cats with live cells infected with FeLV and thereby to induce the development of high levels of anti-FeLV associated antibody in the blood stream. As will be shown below, such levels of antibody are capable of protecting a cat against subsequent infection by the virus.

EXAMPLE 2

Cats vaccinated with a vaccine comprising live cells containing FeLV are capable of withstanding infection when challanged with a high dose of virulent virus.

Three cats, whose sera initially contain no detectable antibody, are each inoculated subcutaneously with $3 \times 10^7$ live feline lymphoblastoid cells chronically infected with FeLV, of low infectivity for cats and feline tissue culture. The cats are bled monthly for serum samples and the results of the immunofluoresence antibody test for anti-FeLV associated antibody are shown in FIG. 2.

The antibody titre rises within the first month to a mean of 256 and all cats reach this antibody level. One month after inoculation the cats are challenged by injection with $10^6$ infectious units of strain FeLV5 virus, known to be highly leukemogenic and pathogenic in cats. The cats are sacrificed and necropsied three months after challenge. The following investigation demonstrates that there is no remaining viral infection resulting from the challenge.

1. No pathological or histological abnormalities are found.
2. No virus is found by electron microscopic examination of bone marrow or tracheal tissue.
3. Plasma from challenged cats is used to inoculate cultures of feline embryo monolayer cells and no virus is detected in the culture.
4. Bone marrow cells are co-cultivated with feline embryo monolayer cells and no infection with virus can be detected.

Similar, but unvaccinated, cats are also challenged with the same dose of infectious FeLV. They are killed and necropsied at the same time as the vaccinated cats and the same tests are applied for virus detection. However, virus particles are detected in all samples tested from these cats. The presence of live virus particles would lead in due course to symptoms of the particular diseases caused by FeLV infection. Vaccination of cats with live cells containing FeLV of low infectivity therefore produces in those cats an immunity against subsequent infection with virulent FeLV.

EXAMPLE 3

Cats may be treated with a vaccine in which the virus-containing cells are killed by treatment with paraformaldehyde.

Feline lymphoblastoid cells ($2 \times 10^8$), chronically infected with FeLV of low infectivity, are suspended in 1 ml. Hank's solution. 9 ml. of 1% paraformaldehyde is added slowly while the mixture is stirred on an ice bath. The cells were kept in paraformaldehyde at 4°C. for one hour and then washed in Hank's solution. Aliquots were prepared each containing $6 \times 10^7$ cells in 1 ml. of solution.

Cats, having no detectable FeLV antibodies in their sera, are injected subcutaneously with an aliquot containing the killed cells prepared above. They are bled monthly for serum samples and the anti-FeLV antibody titres are shown in FIG. 3.

High antibody titres are reached within three months of vaccination and persist for 3–4 months at which time the animals are killed. The same techniques described in Example 1 for the detection of virus particles are applied to all animals and no virus particles are detected.

A high antibody titre, shown in Example 2 to protect cats against infection with live FeLV, may be stimulated in cats by vaccination with virus-containing cells killed by treatment with paraformaldehyde.

EXAMPLE 4

Animals with an initial anti-FeLV antibody titre of 4 may develop a high antibody titre upon immunization with inactivated infected cells. The initial antibody titre may have resulted from a natural infection or from prior immunization such as that described in Example 2.

An animal with an initial antibody titre of 4 is injected with a vaccine prepared from infected feline embryo fibroblasts cells which have been inactivated with formaldehyde and acetylethyleneimine(AEI). The cells are cultured in monolayer and are infected and harvested as described before. $3 \times 10^8$ cells are suspended in 100 ml of 0.05% formaldehyde for 1 day at 22°C. The cells are again washed twice in buffer and are resuspended in 200 ml of 0.05% AEI for one day at 22°. The cells are again washed and resuspended in 20 ml of buffer to which has been added 2 ml of 20% sodium thiosulphate. The cells are resuspended in 4 ml of buffer and 0.5 ml of the suspension is injected subcutaneously into the animal.

The animal has a pre-inoculation antibody titre of 4. Within one month, the antibody titre is 32 and this is maintained at 3 months. At the end of this period, no virus or virus particles can be detected in the animal by means of electron microscopy or immunofluorescence. It is therefore possible to initiate a strong secondary reaction in an animal having an antibody titre of 4 by injection of infected cells which have been inactivated by means of formaldehyde and AEI. The antibody titres achieved by such immunization are capable of protecting an animal against subsequent infection with FeLV and these antibody levels are maintained for a considerable period of time.

EXAMPLE 5

Immunization capable of inducing protective titres of anti FeLV antibody was achieved by the injection of infected feline embryo cells killed by treatment with formaldehyde. Feline embryo fibroblasts are grown in monolayer culture, infected and harvested as before. The cell suspension is added to 20 times its volume of 1/100 formaldehyde and stored at +4°C. for one week. The cells are centrifuged at 5,000 r.p.m., wahsed and re-suspended in Alsever's Solution. In this form, the cells may be stored at minus 20°C. for two months.

The cells are diluted and $1.5 \times 10^8$ cells per animal are injected subcutaneously into mature adult cats. Peak antibody titres of 16 are achieved within one month of immunization. It is shown below that animals with this titre of antibody are able to successfully resist an infection with live virus by mounting a secondary reaction. In addition, no trace of virus or virus antigen could be detected by microscopy of the tissues of animals immunized by this procedure.

EXAMPLE 6

Animals in which there is a detectable antifeline leukemia virus antibody titre are capable of developing a strong secondary response to infection with live virus which is capable of overcoming the virus and eradicating the infection.

Animals with an initial antibody titre of 16, together with some animals with no detectable antibody titre, are injected with a high dose ($10^{10}$ particles per animal) of live FeLV.

Figure 4:
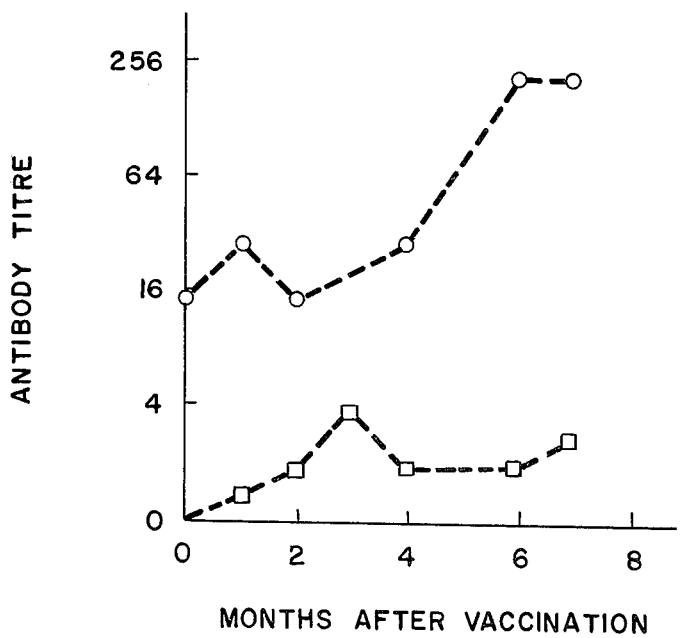

The animals are monitored over a period of 7 months for the levels of anti feline leukemia antibodies in the blood, and these levels are shown in FIG. 4. Those animals which had no detectable antibodies when injected with virus became chronically infected and contracted many of the diseases associated with FeLV. In addition, many died. In contrast, those animals having an initial antibody titre of 16 developed a strong secondary reaction to the injected virus and after 6 months displayed an antibody titre of 256. There was no detectable disease or virus in these latter animals at the end of 7 months. It is clear therefore that animals with a relatively low initial antibody titre are capable of mounting a strong secondary reaction to infection with live virus.

EXAMPLE 7

A vaccine is prepared from virus separated from cells in which it is grown. Cats innoculated with such a virus raise titres of anti FeLV antibodies which allow them to subsequently resist infection with live virus by mounting a strong secondary immunological response.

Infectious FeLV particles are grown in FEA monolayer cells and separated from the cells by conventional techniques of ammonium sulphate precipitation and density gradient centrifugation. The virus particles are added to the inactivating agent at the concentration given below and incubated for 6 hours at 4°C. The inactivation by AEI was stopped by the addition of 20% sodium thiosulphate. One part of Freund's incomplete adjuvant was added to each part of the virus suspension.

Cats are innoculated with approximately $10^7$ virus particles and the peak antibody titre reached within three months was recorded. It is shown in Table 2 that cats injected with inactivated virus subsequently produce moderate antibody titres against FeLV. These titres are such that a subsequent innoculation or injection would result in a strong secondary response with the production of high antibody titres.

The animals were sacrificed after three months and samples of tissue and blood are examined by electron microscopy, immunofluorescence, and cocultivation with uninjected cells. No virus particles are detected.

TABLE 2

| Inactivant | Response — mean peak antibody titre |
|---|---|
| Formalin (0.05%) | 11.3 |
| AEI (0.05%) | 4 |
| Formalin (0.05%) + AEI (0.05%) | 5.7 |

NB. All injections included Freund's incompleted adjuvant (50%).

What is claimed is:

1. A vaccine for the prevention of diseases caused by Feline leukemia virus which comprises in unit dosage form about $10^7$–$10^9$ cells infected with live Feline leukemia virus said cells having virus-associated antigen or their surface.

2. A vaccine according to claim 1 which comprises feline cells infected with Feline leukemia virus.

3. A vaccine according to claim 1 which comprises feline embryo cells infected with Feline leukemia 4. A method for protecting cats against diseases caused by Feline leukemia virus which comprises administering to the cat, by injection, the vaccine of claim 1.

* * * * *